(12) United States Patent
Trott et al.

(10) Patent No.: US 7,442,345 B2
(45) Date of Patent: Oct. 28, 2008

(54) REACTOR APPARATUS

(75) Inventors: Louis R. Trott, Naperville, IL (US); David R. Wagner, Naperville, IL (US); Steven J. Rowe, Geneva, IL (US); Robert A. Gustaferro, Naperville, IL (US); Gregory A. Norenberg, Medina, OH (US); Kenneth P. Keckler, Naperville, IL (US); Robert P. Hepfer, St. Charles, IL (US)

(73) Assignee: Ineos USA LLC, Lisle, IL (US)

( * ) Notice: Subject to any disclaimer, the term of this patent is extended or adjusted under 35 U.S.C. 154(b) by 460 days.

(21) Appl. No.: 10/840,855

(22) Filed: May 7, 2004

(65) Prior Publication Data

US 2005/0002837 A1    Jan. 6, 2005

Related U.S. Application Data

(60) Provisional application No. 60/469,608, filed on May 9, 2003.

(51) Int. Cl.
*B01J 8/24* (2006.01)

(52) U.S. Cl. .................. 422/146; 422/147; 422/143; 422/139

(58) Field of Classification Search ................. 422/146
See application file for complete search history.

(56) References Cited

U.S. PATENT DOCUMENTS

| | | | | |
|---|---|---|---|---|
| 2,518,270 | A * | 8/1950 | Barr .......................... 422/146 |
| 2,546,570 | A * | 3/1951 | Vance, Jr. .................... 518/728 |
| 2,585,274 | A * | 2/1952 | Reichl ......................... 422/143 |
| 2,665,288 | A * | 1/1954 | Odell .......................... 518/707 |
| 3,042,498 | A * | 7/1962 | Norman ....................... 422/143 |
| 3,472,892 | A | 10/1969 | Callahan et al. .......... 260/465.3 |
| 3,615,256 | A | 10/1971 | Miller et al. ............... 23/288 S |
| 3,639,103 | A | 2/1972 | Sheely ......................... 23/288 |
| 3,974,091 | A * | 8/1976 | Parker et al. .................. 502/41 |
| 4,062,656 | A * | 12/1977 | Blaser et al. .................... 48/73 |
| 4,096,909 | A | 6/1978 | Jukkola |
| 4,158,036 | A | 6/1979 | Jaffe et al. |
| 4,391,880 | A | 7/1983 | Tsao .......................... 423/659 |
| 5,256,810 | A * | 10/1993 | Rowe et al. ................... 558/320 |
| 6,358,483 | B1 | 3/2002 | Trott et al. .................... 422/231 |

FOREIGN PATENT DOCUMENTS

| | | |
|---|---|---|
| DE | 1 442 760 | 7/1963 |
| EP | 0 446 379 A1 | 9/1991 |
| EP | 0 599 460 A1 | 6/1994 |

(Continued)

OTHER PUBLICATIONS

Acrylonitrile Reactor Cyclone System, Gary Kissel, Fisher-Klosterman, Inc., Hydrocarbon Engineering, Dec./Jan. 1998/1999, pp. 53-54.

*Primary Examiner*—Jennifer A Leung
(74) *Attorney, Agent, or Firm*—David P. Yusko; Vik Panchal

(57) ABSTRACT

A new reactor apparatus that can be used to carry out chemical reactions in a fluidized catalyst bed at high temperatures with reduced afterburning or other undesirable downstream side reactions.

16 Claims, 8 Drawing Sheets

FOREIGN PATENT DOCUMENTS

| | | |
|---|---|---|
| EP | 1202017 A | 5/2002 |
| FR | 937899 A | 8/1948 |
| GB | 1 365 135 | 11/1971 |
| GB | 2 075 360 | 4/1981 |
| JP | 02019370 A * | 1/1990 |
| WO | WO 96/03478 A1 | 2/1996 |
| WO | WO 96/23582 | 8/1996 |
| WO | WO9626003 A | 8/1996 |
| WO | WO 99/34907 | 7/1999 |

* cited by examiner

REACTOR APPARATUS

This application claims the benefit of U.S. Provisional Patent Application Ser. No. 60/469,608, filed on May 9, 2003.

This invention relates to new reactor apparatus useful for carrying out chemical reactions. More particularly, this invention relates to new reactor apparatus that can be used to carry out chemical reactions in a fluidized catalyst bed. Still more particularly, this invention relates to new reactor apparatus that can be used to carry out chemical reactions in a fluidized catalyst bed at high temperatures and in the gas phase with reduced afterburning or other undesirable downstream side reactions of products and residual reactants.

BACKGROUND OF THE INVENTION

Acrylonitrile is an important commodity chemical used mainly as monomer for the manufacture of a wide variety of polymeric materials such as polymers for acrylic fibers used, for example, in textiles, and in resins, such as ABS and SAN resins. Worldwide, acrylonitrile is produced in amounts exceeding four million metric tons per year. One method for manufacturing acrylonitrile is to oxidize propylene in the presence of ammonia using air or other source of molecular oxygen as the oxidant. Such oxidation reactions, also called ammoxidation reactions, typically use a solid-particulate heterogeneous catalyst in a fluidized catalyst bed to catalyze the ammoxidation reaction and provide the desired acrylonitrile in acceptable conversion and yield. In addition to producing acrylonitrile, such ammoxidation reactions also generally produce hydrogen cyanide and other valuable co-products.

While propylene is a desirable feedstock for such ammoxidation reactions to produce acrylonitrile, it would be desirable to be able to use a less expensive feedstock such as propane. Heterogeneous catalyst materials have been developed which can be used to convert propane to acrylonitrile using a fluid bed reactor and oxygen gas, for example, as the oxidant. However, in such reactions where propane is mixed with ammonia and air, oxygen gas, or other source of molecular oxygen, and reacted at elevated temperature in the presence of a fluidized bed of particulate catalyst, hot product gases continue to oxidize after the product gases leave the catalyst bed. Such uncontrolled oxidation downstream of the fluidized catalyst bed, also referred to as afterburning, results in a loss of valuable feed material, such as propane, which could otherwise be recycled, as well as a loss of valuable products, such as acrylonitrile. Thus, it would be desirable to have a reactor apparatus and process that can be used to reduce the amount of such uncontrolled downstream oxidation or other undesirable side reaction and the loss of products and feed materials. The present invention provides such reactor apparatus and process.

SUMMARY OF THE INVENTION

This invention is a reactor apparatus comprising a reactor vessel comprising a first zone, at least a second zone, and a catalyst separator apparatus, the first zone comprising at least one inlet for a reactant and the second zone comprising a gas cooler located at least partially within the reactor vessel suitable for cooling gases passing through the gas cooler. The reactor apparatus of this invention can be used, for example, for the ammoxidation of propane to acrylonitrile.

This invention is also a process for reacting in a reactor vessel at least one reactant gas phase component in the presence of a solid, catalytic material to form at least one product gas phase component comprising contacting at least one reactant gas phase component in the presence of a particulate catalyst material under conditions which form a fluidized bed of particulate catalyst and at least one product gas phase component, directing a mixture comprising at least a portion of the product gas phase component and particulate catalyst from the fluidized catalyst bed suspended therein to a cooler located at least partially within the reactor vessel, cooling the mixture, separating suspended catalyst from the mixture after cooling to form separated catalyst and a gas phase comprising at least one gas phase product component, and returning at least a portion of the separated catalyst to the fluidized catalyst bed.

DESCRIPTION OF THE PREFERRED EMBODIMENT(S)

Figure 1:
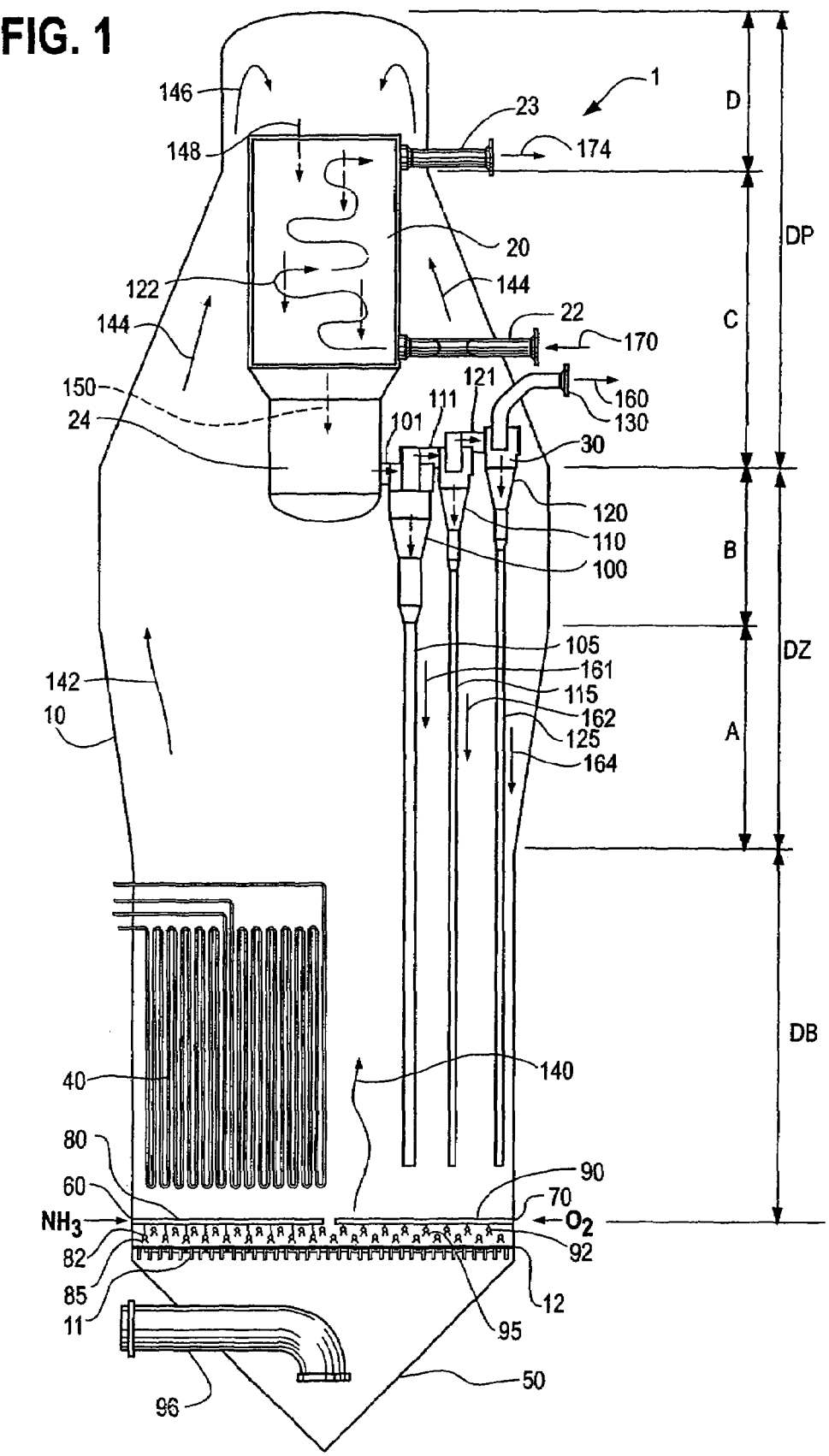
FIG. 1 shows in cross-sectional view a preferred reactor apparatus of this invention.

The reactor apparatus of this invention comprises a reactor vessel or shell suitably constructed of a material that can withstand temperatures and pressures used to conduct a desired chemical reaction therein. It is desirably constructed of, or at least has an internal lining made of, a material that will withstand the chemical reactivity of the chemical compounds or other materials contained therein, particularly at elevated reaction temperatures and pressures. Thus, the material selected should not corrode or at least not corrode rapidly while in use. The material used to construct the reactor vessel or lining is also preferably abrasion resistant so it can withstand abrasion caused by hard, particulate catalyst used, for example, in a fluidized catalyst bed. Thus, the reactor shell or vessel can be constructed of a steel such as low alloy steel, stainless steel, or carbon steel. The shape of the reactor vessel is preferably, generally cylindrical, that is, the horizontal cross-section of the vertically positioned reactor vessel is circular. Since the chemical reactions performed in the reactor vessel are generally conducted at an elevated pressure, it is desirable for the ends of the reactor vessel to be capped using, for example, a conical or a domed cap. The domed shaped cap can, for example, be hemispherical or elliptical. However, the caps for the ends of the reactor vessel can have any suitable shape. Although the reactor vessel can have the same width or diameter along its entire length, it can, as will be described in more detail below, have a width or diameter that varies along its length. For example, the generally cylindrically shaped vessel can have a larger diameter at one end and a narrower diameter at the other end. In one of the preferred embodiments of this invention, the reactor has a middle section or zone that is of an expanded or larger diameter than the bottom section or zone and a top section or zone that is narrower than the bottom section or zone. If cylindrically shaped, the reactor apparatus of this invention, depending on the application it will be used for, can have at its widest diameter a diameter of about 5 to about 100 feet, preferably about 8 to about 50 feet.

The reactor apparatus of this invention preferably has at least two, and more preferably at least three zones or sections. When the reactor apparatus is positioned vertically, which is the preferred orientation, the first or lower or bottom zone is referred to as the dense bed zone, the second or middle zone is referred to as the disengaging zone, and the third, or upper, or top zone is referred to as the dilute phase zone. By positioned vertically, we mean the axis, for example, the axis of a generally cylindrical reactor vessel, is in a vertical position. The dense bed zone is the location in the reactor apparatus where a particulate catalyst is contacted with reactant gas or gases entering the reactor apparatus to form a fluidized bed of catalyst. The disengaging zone is the location in the reactor apparatus where the particulate catalyst from the fluidized bed is, for the most part, separated from the gas mixture comprising product gas or gases exiting the fluidized catalyst bed. In the disengaging zone product gas or gases exiting the dense bed zone move in an upward direction in the vertically positioned reactor and, due to gravity, most of the catalyst particles entrained or suspended in the product and, if present, unreacted reactant gas or gases exiting the fluidized catalyst bed fall and return to the dense portion of the fluidized catalyst bed while the product gas or gases containing the remaining amount of suspended or entrained catalyst particles continue upward into the dilute phase zone. In the dilute phase zone, the product gas or gases containing the suspended or entrained catalyst particles are cooled by a gas cooler and thereafter the suspended or entrained catalyst particles are separated from the product gas or gases using a catalyst separation apparatus, such as a gas-solids cyclone or series of gas-solids cyclones, and the catalyst particles separated are preferably returned to the fluidized catalyst bed in the dense bed zone. In the process of this invention, the suspended or entrained catalyst in the gas or gases exiting the disengaging zone can be used to reduce or eliminate afterburning or other undesirable side reaction that would otherwise occur if the catalyst particles were not present. In the preferred process of this invention, the suspended catalyst particles are separated from such gas or gases only after the mixture comprising the gas or gases and the suspended or entrained catalyst is cooled to a temperature below which afterburning or other undesirable side reaction is eliminated or at least reduced to an acceptable level.

The dense bed zone of the reactor apparatus of this invention preferably comprises a metal plate that can be used to support catalyst particles of a fluidized bed of catalyst during, for example, intervals such as a reactor start up or shut down when the catalyst bed is in a quiescent, that is, non-fluidized state. The plate preferably extends across the entire diameter of the reactor vessel. In the preferred reactor apparatus of this invention the plate is in the form of a grid. By grid, we mean a plate having a collection of perforations or holes, preferably round holes, that will permit the passage of a gas from one side of the grid to the other. When the reactor is in the preferred vertical position, the grid is preferably near the bottom of the reactor vessel so that there is a space or void located below the grid but within the reactor vessel. This space can be used to introduce a reactant gas into the reactor such as, for example, propane. It can be fresh propane, recycled propane or both, if the reactor is used for the reaction of propane with ammonia and a source of molecular oxygen to form acrylonitrile. The thickness of the grid and the number and diameter or size of the holes can vary. However, generally, there can be about 0.1 to about 3 holes per square foot of grid area. The grid can have a thickness of up to about 1.25 inch, for example, about 0.5 inch to about 1.25 inch. The holes in the grid are preferably arranged in parallel, preferably evenly spaced rows. The holes in one row are preferably offset from, for example between the holes, in the adjacent rows. The holes in the grid can be fitted with nozzles or tubular gas inlets that extend down from the surface of the upper portion of the plate to a location below the plate. The nozzles preferably have a smaller diameter orifice located therein and preferably at the end of the nozzle away from or distal from where the nozzle is attached to the grid. The holes in the grid and the orifices in the nozzles are preferably sized to provide for an even distribution of gas across the horizontal cross-section of the reactor apparatus and a gas flow velocity sufficient to prevent or reduce the backflow of any reactant gases or catalyst particles into the space below the grid. The grid can be made of the same material as the reactor vessel. As discussed in more detail below, it is preferable to have a layer of refractory insulating material on the side of the grid that is facing the portion of the reactor vessel where the fluidized catalyst bed is located. The refractory insulating material prevents the grid from reaching temperatures high enough to cause excessive degradation or combustion of the reactant gases such as propane beneath the grid, particularly if molecular oxygen gas is present. The refractory insulating material can have a thickness of up to 6 inches, such as about 2 inches to about 6 inches. The refractory material can be selected from any suitable material that will be generally inert under the reaction conditions used in the reactor. For example, it can be one or more of a ceramic fiber or an alumina silicate, or other material that provides suitable high temperature stability, insulation, chemical resistance and thermal shock resistance. The layer of refractory insulating material has holes, preferably of the same size as the holes in the grid. The holes in the layer of refractory insulating material are positioned over holes in the grid. The nozzles for the grid, if used, can extend to the top of the layer of refractory insulating material.

The dense bed zone of the preferred reactor apparatus of this invention preferably comprises a reactant gas distribution system or sparger for delivering the reactant gases such as, for example, ammonia and a molecular oxygen-containing gas to the reactor apparatus. In the preferred reactor apparatus, a reactant gas is distributed by a collection or plurality of distribution tubes positioned near the grid. The size and number of tubes may vary and will be selected depending, for example, on the volume of gas to be distributed and the rate of such delivery desired. The tubes are preferably in a parallel arrangement across and near the surface of the grid that faces the fluidized catalyst bed. Attached to and extending from each distribution tube in a direction preferably toward the grid are a plurality of delivery tubes that are preferably of a shorter length and smaller diameter than the distribution tubes. The delivery tubes preferably extend downward from the distribution tubes and at an angle from vertical. A reactant gas flowing through the distribution tubes is directed by these delivery tubes to a location at or near the surface of the grid. The delivery end of the delivery tube, that is, the end of the delivery tube away from where it connects to the distribution tube, can be up to about 18 inches, for example, about 3 inches to about 18 inches from the surface of the grid. Each of the distribution tubes is connected to one or more manifold tubes. Preferably, the manifold tubes are of a larger diameter than the distribution tubes. In the preferred operation of the reactant gas distribution system, reactant gases entering the manifold tubes flow to the distribution tubes, and from the distribution tubes to the delivery tubes, and from the delivery tubes into the reactor vessel to a location near the holes in the grid.

The distribution tubes can be positioned so they are above the spaces between rows of holes in the grid. There may be one or more independent reactant gas distribution systems, each comprising a manifold tube or tubes, distribution tubes and delivery tubes, for each reactant gas. For example, there may be one or more of such reactant gas distribution systems for each of ammonia gas and oxygen-containing gas, such as air or molecular oxygen gas for a reactor apparatus used for the ammoxidation of propane. Preferably, at least one end of each manifold tube extends through the wall of the reactor so that a connection can be made for the delivery of the reactant gas to the manifold external to the reactor. The manifold tubes are preferably insulated with a suitable insulating material. The distribution tubes are preferably insulated with a suitable insulating material. The delivery tubes are preferably insulated with a suitable insulating material. Preferably, the manifold tubes, distribution and delivery tubes are insulated with a suitable insulating material. The insulating material is preferably a material that will withstand the high temperatures within the fluidized catalyst bed while providing suitable insulation, chemical resistance, and thermal shock stability. Preferably it is in fibrous form. The insulating material is added to prevent the internal temperature of the manifold, distribution and delivery tubes from reaching temperatures high enough to cause excessive degradation of either the gas contained therein or the material used to manufacture the tube. In turn, the insulating material can be contained within an outer jacket constructed of a material such as steel to help stabilize and protect the insulation. U.S. Pat. No. 6,385,483, which is incorporated herein by reference in its entirety, discloses insulated and jacketed spargers useful for sparging oxygen and other gases into the reactor apparatus of this invention. Although described above as tubes, it is understood that the manifold, distribution and delivery tubes can be other shaped conduits.

In the preferred reactor apparatus of this invention, for example, one that can be used for the ammoxidation of propane with ammonia and source of molecular oxygen, there is at least one separate reactant gas distribution or sparger system or systems for molecular oxygen-containing gas and for ammonia gas. In such reactor apparatus, it is preferable to have the delivery tubes of the gas distribution system or systems for the ammonia gas be positioned so that the ends of the delivery tubes where the ammonia gas exits are located directly above or near a hole in the grid, and to have the delivery tubes for the gas distribution system or systems for the molecular oxygen-containing gas be positioned so that the ends of the delivery tubes where the molecular oxygen-containing gas exits are away from a hole in the grid, for example, directly between holes in the grid. With such an arrangement, when a reactant gas, such as propane, is directed through the holes in the grid and into the fluidized catalyst bed, the propane gas first contacts, and is preferably at least somewhat diluted with, ammonia rather than molecular oxygen-containing gas. Such an arrangement provides for a decreased amount of undesirable burning of the propane feed.

The dense bed zone of the preferred reactor apparatus of this invention preferably comprises one or more heat transfer apparatus that can be used for adding or preferably removing heat from a fluidized catalyst bed. The heat transfer apparatus can be any suitable means for adding or removing heat from a fluidized catalyst bed. Most preferably, the heat transfer apparatus comprises at least one and more preferably a collection of tubes, preferably in a coiled or looped configuration, that have a suitable heat transfer medium, such as, for example, water, steam or a molten salt or salts, circulating through the tubes. Another heat transfer apparatus can be, for example, a liquid vaporizer. By liquid vaporizer we mean an apparatus that uses the heat generated by an exothermic chemical reaction in the fluidized catalyst bed to vaporize one or more liquids, such as liquid ammonia or propane, for the ammoxidation of propane to form acrylonitrile. Thus, in a liquid vaporizer the heat is transferred from the fluidized catalyst bed to the liquid to be vaporized by, for example, passing the liquid through one or more tubes positioned within the fluidized catalyst bed. The heat of the reaction in the fluidized catalyst bed vaporizes the liquid.

The heat transfer apparatus can be used to regulate the temperature of a fluidized catalyst bed used to conduct exothermic reactions such as the ammoxidation of propane using ammonia and source of molecular oxygen. The regulation can be accomplished by controlling the rate of flow of heat transfer medium through the heat transfer apparatus or by having multiple heat transfer apparatus and having a predetermined number in service to achieve the desired temperature conditions within the fluidized catalyst bed. The heat transfer apparatus is preferably constructed of a material that can, like the reactor vessel, withstand the conditions of high temperatures and pressures, abrasive particulate catalysts and possibly corrosive feed or product components. Thus, like the reactor vessel, the heat transfer apparatus is preferably constructed of materials such as, for example, low alloy steel, stainless steel or carbon steel.

The second or disengaging zone in the preferred reactor apparatus of this invention is the section of the reactor apparatus where catalyst particles from the fluidized catalyst bed that have become suspended or entrained in the mixture comprising product and, if present, reactant gases exiting the fluidized catalyst bed, separate or disengage in part from such product and, if present, reactant gases. In the preferred vertical arrangement of the reactor apparatus of this invention, the fluidized catalyst bed is contained mostly or, preferably, completely in the lower, dense bed zone of the reactor apparatus. In the fluidized bed, catalyst particles are mixed with a reactant gas or gases while the catalyst in the fluidized bed is catalyzing the chemical reaction of the reactant gas or gases to form product or products. In the preferred embodiment of this invention, the reactant gas or gases enter the reactor vessel at a point below or near the bottom of the catalyst bed and it is preferably the flow of the gas or gases that causes the catalyst particles in the bed to mix and fluidize. For example, as a gas mixture comprising product and, if present, reactant gases moves up through the fluidized catalyst bed in a generally upward direction and exits the fluidized catalyst bed, a portion of the catalyst particles from the bed is suspended or entrained in the mixture comprising product and, if present, reactant gases. This mixture comprising the gas or gases and suspended or entrained catalyst particles enters the disengaging zone where most, but not all, of the entrained or suspended catalyst particles returns to the catalyst bed by gravity. In the preferred reactor apparatus of this invention, the disengaging zone comprises an open space or volume in the reactor vessel located generally in the center or middle section of the vertically positioned reactor vessel. The size of the disengaging zone can be selected based on the type of reaction to be conducted in the reactor apparatus. For the preferred reaction of propane with ammonia and source of molecular oxygen to produce acrylonitrile, as well as for other chemical reactions, it is desirable for a certain amount of the particulate catalyst to remain suspended or entrained in the mixture of product and, if present, reactant gases exiting the disengaging zone until such mixture of suspended or entrained catalyst particles, product and, if present, reactant gases is cooled to a suitable temperature. The entrained catalyst particles eliminate or reduce the amount of undesirable destructive afterburning or other undesirable side reaction that would otherwise occur. The amount of suspended or entrained catalyst can be about 0.05 to about 2.0 pounds per pound of the gas mixture comprising product and, if present, reactant gases. Thus, if an insufficient amount of catalyst is contained within the mixture comprising product and, if present, reactant gases exiting the disengaging zone, there can be excessive afterburning or other undesirable side reaction, which will reduce the yield of the desired product or products, such as acrylonitrile, and a feed gas, such as propane, that could otherwise be separated and recycled for conversion to desired product. If the amount of entrained catalyst is excessive, such catalyst, which is cooled with the mixture of product and, if present, reactant gases so it can be returned to the fluidized catalyst bed, can cause an excessive cooling of the fluidized catalyst bed. Therefore, it is necessary to control the amount of suspended catalyst in the gas exiting the disengaging zone so that there is a sufficient amount in the mixture to control afterburning or other undesirable side reaction to an acceptable level, but not have an amount so that after cooling it and returning it to the fluidized catalyst bed, it excessively cools the fluidized catalyst bed. The amount of catalyst present in the product and, if present, reactant gases exiting the disengaging zone can be controlled by the size and density of the catalyst particles used in the fluid bed reactor, the rate of flow of reactant gas into the fluidized catalyst bed, and by the length and particularly the diameter of the disengaging zone. By length we mean in a vertically positioned reactor, the vertical length of the disengaging zone. Thus, in the preferred reactor of this invention the disengaging zone is suitably about 100 to about 150 percent the length of the dense bed zone. While the disengaging zone of the reactor apparatus of this invention can be the same as the diameter of the dense bed zone, preferably the disengaging zone can have an expanded or increased diameter relative to the largest diameter of the dense bed zone. For example, at its greatest diameter, the disengaging zone can have a diameter that is about 5 percent to about 100 percent greater than the diameter of the dense bed zone, more preferably about 15 to about 20 percent greater. Thus, the reactor vessel of the reactor apparatus of this invention, when in a vertical position, can have a tapered section starting at about the upper end of the dense bed zone with the taper expanding to a larger diameter into the disengaging zone.

The reactor apparatus design of this invention having a middle section or disengaging zone that is larger diameter than the dense bed zone provides for a more compact reactor apparatus and, compared to the reactor apparatus having a dense bed zone and disengaging zone of the same diameter, it also provides for higher gas velocities in the dense bed zone which can improve contact between the reactant gas or gases and the solid, particulate catalyst contained therein resulting in more efficient catalytic reaction.

As will be discussed in greater detail below with reference to FIG. 11, another suitable method for controlling or adjusting the amount of catalyst particles present in the mixture comprising product and, if present, reactant gases exiting the disengaging zone is to use one or more catalyst separation apparatus, such as a filter, or more preferably, a gas-solids separating device, such as a gas-solid cyclone, to separate the catalyst and preferably return a portion of the suspended or entrained catalyst to the fluidized bed. In the case of a cyclone, a mixture of gases comprising product and, if present, reactant gases exiting the fluidized catalyst bed and containing suspended or entrained catalyst particles is passed into the intake of one or more cyclones to remove a desired amount of catalyst from the gas mixture and return the catalyst to the fluidized catalyst bed. Such a catalyst separation apparatus can be located outside or more preferably inside the reactor vessel.

The third or dilute phase zone in the preferred reactor apparatus of this invention is the section of the reactor apparatus where, preferably, the mixture comprising product and, if present, reactant gases and suspended or entrained catalyst particles exiting the disengaging zone is cooled by one or more suitable gas cooling apparatus. The cooling can be accomplished, for example, by passing the mixture through another bed of catalyst of the same or different composition as the catalyst used in the fluidized catalyst bed. Preferably, it is a catalyst bed of the same composition as used for the fluidized catalyst bed. Such cooling catalyst bed should be of a sufficient size to achieve the desired cooling. The cooling catalyst bed may also contain one or more heat transfer apparatus such as the heat transfer apparatus described above for use in the fluidized catalyst bed. Such heat transfer apparatus can be used to regulate the temperature of the cooling catalyst bed to the desired temperature during the operation of the reactor apparatus.

Preferably, the gas cooling apparatus is a shell-and-tube gas cooler and is located at least partially and preferably totally within the reactor vessel and at least partially, preferably mostly, and more preferable totally within the dilute phase zone or section of the reactor apparatus. In such shell-and-tube gas cooler, the mixture comprising product and, if present, reactant gases and suspended catalyst particles is passed through a plurality of tubes, where the tubes are jacketed by a closed shell. Within the shell but outside the tubes, a suitable heat transfer medium or fluid is circulated to remove heat from the tubes thereby cooling the gas and catalyst particles flowing through the tubes. The fluid flowing through the shell-and-tube cooler can be, for example, water, a low melting salt or salt eutectic, a low melting metal, and the like. Preferably the shell contains therein a plurality of baffles or other such devices to provide for a turbulent flow of the fluid within the shell so that the fluid reaches and thereby removes heat from all the cooling tubes located therein.

In the preferred reactor apparatus of this invention, the gas cooling apparatus is positioned at or near the top of the reactor apparatus when the reactor apparatus is positioned in the preferred vertical orientation. The mixture exiting the disengaging zone of the reactor and comprising product and, if present, reactant gases as well as suspended or entrained catalyst particles can pass through the cooling apparatus, such as the shell-and-tube gas cooler, as the mixture proceeds vertically through the reactor apparatus. It can move past the gas cooling apparatus as it proceeds vertically through the reactor apparatus, be directed down by the cap at the top end of the reactor vessel, and then pass through the cooling apparatus on a path downward through the gas cooling apparatus. Alternatively, it can pass through the cooling apparatus in both the upward and downward direction. In the preferred reactor apparatus of this invention, the gas cooling apparatus, preferably in the form of a shell-and-tube gas cooler, is positioned within the reactor vessel so that the mixture comprising product and, if present, reactant gases, and entrained catalyst particles passes around the cooling apparatus as the mixture proceeds vertically up through the reactor vessel, the mixture turning to proceed in the reverse direction as it reaches the cap at the end of the reactor vessel, and then passing through the cooling apparatus as it progresses downward through the cooling apparatus. Thus, in the reactor apparatus of this invention the gas cooler can be an upflow single-pass shell-and-tube gas cooler where the gases comprising suspended catalyst particles pass through the cooler on the path upwards within the reactor apparatus, a downflow single-pass shell-and-tube cooler where the gases comprising suspended catalyst particles pass through the gas cooler on the path downwards within the reactor apparatus, or a two-pass shell-and-tube gas cooler where the gases comprising suspended catalyst particles are passed through the shell-and-tube cooler on their path upwards within the reactor and then pass through the shell-and-tube cooler again on the path downwards within the reactor. Another gas cooling apparatus comprises using one or more cooling coils located within the reactor in the path of the gas, preferably in the top zone of the reactor apparatus of this invention. The cooling coil or coils have a heat transfer medium or fluid, such as a liquid or gas, circulating therein to remove heat from the mixture of reactant and product gases and suspended catalyst. The cooling coil or coils can be used alone or in combination with another gas cooling apparatus such as either of the described single-pass shell-and-tube gas coolers, or the two-pass shell-and-tube gas cooler.

In the preferred reactor apparatus of this invention, the top zone of the reactor vessel, or at least a portion thereof, is smaller in diameter than the disengaging zone. More preferably, the top or dilute phase zone of the reactor apparatus, or at least a portion thereof, is smaller in diameter than the dense bed zone. For example, the dilute phase section or zone of the reactor apparatus, or at least a portion thereof, can have a diameter that is about 5 percent to about 100 percent, more preferably about 25 to about 75 percent of the diameter of the dense bed zone of the reactor vessel. The smaller diameter reactor top increases the velocity of the gas, thereby reducing the residence time of the gas and reducing the amount of any undesirable chemical reactions, such as afterburning, that might occur at high temperatures.

As stated above, the cooling apparatus can be used to lower the temperature of the mixture comprising the product, suspended catalyst particles and, if present, reactant gases. After the temperature of such mixture is lowered to a suitable temperature where appreciable afterburning, or other undesirable side reaction, will not occur, the catalyst can be separated from the mixture. If the catalyst is not separated from the mixture it will be carried out of the reactor apparatus with the product and, if present, reactant gases and result in an undesirable loss of catalyst, which may cause handling and disposal problems thereafter. Therefore, in the preferred reactor apparatus of this invention one or more catalyst separation apparatus is used to separate the entrained catalyst from the mixture of product and, if present, reactant gases exiting the cooling apparatus. Any suitable apparatus for performing such separation can be used, such as filters, membranes, screens and other similar apparatus that permit the gases to pass through but prevent or at least retard the passage of the catalyst particles so that a separation of the solids from the gases can occur. The separation apparatus, or plurality thereof, are preferably located at least partially, and more preferably totally, within the reactor vessel. The preferred catalyst separation apparatus used in the reactor apparatus of this invention is a gas-solids separating cyclone, preferably a series, or stages of connected cyclones to efficiently separate the catalyst particles from the mixture. Suitable cyclones are commercially available. In the preferred reactor apparatus of this invention, a plurality of such cyclones, preferably three, are connected in series. With such a series arrangement, more than about 99 percent, for example, about 99.9 to about 99.999 weight percent of the particulate catalyst present in the mixture comprising product, suspended catalyst particles and, if present, reactant gases entering the series arranged cyclones is separated from such mixture thereby providing for an effluent gas stream having, preferably, less than about 0.1, more preferably less than about 0.01, and most preferably less that about 0.002 weight percent catalyst particles.

The number of groups of such series arranged cyclones and the size and a specific shape of such cyclones are selected to provide the desired degree of separation of catalyst particles from the mixture of product and, if present, reactant gases. For example, about 2 to about 20 groups of about 2 or 3 or more cyclones in series can be used.

After the catalyst particles are separated from the mixture comprising product, catalyst particles and, if present, reactant gases, the separated catalyst particles are preferably returned to the fluidized catalyst bed reactor. In the preferred reactor apparatus of this invention, such return is accomplished by a dipleg from the gas cyclones extending to or into the fluidized catalyst bed.

After exiting the cooling apparatus but prior to entering the separation apparatus the mixture comprising product and, if present, reactant gases, and suspended or entrained catalyst particles preferably enter a plenum for distributing the mixture of gases and suspended catalyst particles to a separation apparatus, and preferably to a plurality of separation apparatus, for separating the suspended catalyst particles from the gas. The plenum is preferably a chamber attached to or contiguous with the cooling apparatus.

After exiting the separation apparatus, the gas or mixture of gases is directed by a pipe or other suitable conduit through the reactor vessel wall so the gas mixture can be treated to remove desired product or products and, preferably, reactant components, if present. Any separated reactant components can, if desired, be recycled to the operating reactor apparatus for conversion to products.

The reactor apparatus of this invention is particularly suited for conducting chemical transformation reactions using a fluidized catalyst bed to catalyze a desired chemical reaction. The reactor apparatus of this invention is preferably used for the ammoxidation of propane using ammonia gas and air, molecular oxygen gas or other source of oxygen-containing gas catalyzed by a fluidized catalyst bed. Such ammoxidation reactions are suitably conducted at a temperature of about 350° C. to about 700° C., more preferably about 400° C. to about 550° C., and at a pressure of no more than about 75 psia, preferably no more than about 50 psia. Oxygen gas is the preferred source of molecular oxygen. An inert gaseous diluent, such as nitrogen, can also be added. The molar ratio of propane-to-ammonia is suitably about 2.5 to about 16, and the mole ratio of molecular oxygen-to-propane is suitably about 1 to about 10. The average catalyst contact time can be about 0.01 to about 10 seconds, preferably about 0.02 to about 10 seconds, and more preferably about 0.1 to about 5 seconds. The catalyst used for the ammoxidation is suitably any solid, particulate catalyst that will catalyze the ammoxidation of propane to form acrylonitrile. Catalysts such as, for example, catalysts disclosed in U.S. Pat. Nos. 6,083,869; 5,866,502; 5,498,588; 5,332,855; 5,258,543; 5,214,016; 5,008,427; 4,788,317; 4,784,979; 4,746,641; 3,860,534 and 3,681,421, which are incorporated herein by reference in their entirety, can be used. Catalysts disclosed in U.S. Pat. Nos. 6,143,916; 6,143,690 and 5,750,760, which are incorporated herein by reference in their entirety, also contain examples of catalysts that can be used.

The composition of the gases exiting the fluidized catalyst bed during the ammoxidation of propane with ammonia and a source of oxygen typically comprises a mixture of acrylonitrile, unreacted ammonia, unreacted propane, carbon oxides, hydrogen cyanide and various co-products such as acetic acid, acetonitrile, acrolein, acrylic acid and oxazole. The temperature of the mixture of product and reactant gases and suspended catalyst particles exiting the fluidized catalyst bed is typically about 350° C. to about 700° C., i.e., approximately the temperature of the fluidized catalyst bed. As described above, and for the reasons described above, it is desirable to have a certain amount of catalyst particles remaining with the mixture comprising product and reactant gases while at this elevated temperature in order to reduce to acceptable levels any afterburning once this mixture exits the fluidized catalyst bed. As described above, in the disengaging zone immediately above the fluidized catalyst bed, a portion and preferably most of the catalyst particles that are suspended in the mixture comprising product and reactant gases returns to the fluidized catalyst bed. It is desirable that the mixture of product and reactant gases exiting the disengaging zone, which is typically at a temperature of about 470° C. to about 510° C., and typically at a pressure of about 10 psig to about 30 psig, still contain some suspended or entrained catalyst particles to reduce or eliminate afterburning. For example about 5 to about 67 weight percent of such mixture comprising reactant and product gases and suspended catalyst should be catalyst. The mixture of reactant and product gases and suspended catalyst is cooled, using a suitable gas cooler, preferably to a temperature of about 250° C. to about 350° C. prior to separating, as described hereinabove, the suspended catalyst from the mixture. At such temperatures, afterburning of, for example, propane and the acrylonitrile and other products contained in the gases is reduced to acceptable levels.

This invention is a process for the manufacture of acrylonitrile comprising reacting a mixture comprising propane, ammonia and a source of molecular oxygen in a fluidized bed of particulate catalyst to form a gaseous mixture comprising acrylonitrile and entrained particulate catalyst, cooling the gaseous mixture comprising acrylonitrile and entrained particulate catalyst to form a cooled mixture, separating particulate catalyst from the cooled mixture, and returning particulate catalyst separated from the cooled mixture to the fluidized bed of particulate catalyst where, for example, the conditions and other parameters just described above, such as temperatures, pressures, the catalysts and fluidized catalyst bed, reactants such as ammonia, propane, oxygen gas or other source of molecular oxygen, diluents, molar ratios of reactants, catalyst contact times, composition of product gases, disengagement of catalyst particles in the disengaging zone of a reactor from a mixture comprising product and reactant gases exiting the fluidized catalyst bed, the return of the disengaged catalyst particles to the fluidized catalyst bed, the temperature, pressure and amount of catalyst remaining suspended or entrained in the mixture comprising product and reactant gases exiting the disengaging zone of a reactor to reduce or eliminate afterburning, and the temperatures to which such mixture is cooled prior to separating the suspended or entrained catalyst from the mixture of gases comprising product and reactant gases, can be used.

Such a process can be conducted in a reactor apparatus as described herein. However, in such a process the cooling of the gas mixture comprising acrylonitrile and entrained particulate catalyst to form a cooled mixture can be accomplished in a gas cooling apparatus, such as the gas cooling apparatus described herein, located within, at least partially within, or located external to the reactor vessel. If the gas cooling apparatus is located external to the reactor vessel, the mixture comprising acrylonitrile and entrained particulate catalyst can be directed to the externally located gas cooling apparatus by a pipe or other suitable conduit and then, after cooling, the cooled mixture an be directed by a pipe or other suitable conduit to a suitable catalyst separation apparatus, such as a catalyst separation apparatus described herein, for separation of the particulate catalyst from the cooled mixture, and return of the catalyst to the fluidized catalyst bed. Preferably, such catalyst separation apparatus is located within the reactor vessel. Alternatively, the external gas cooling apparatus can be mounted next to or on top of the reactor vessel and the mixture comprising acrylonitrile and entrained particulate catalyst can be directed to the externally located gas cooling apparatus without the need of a pipe or conduit. For example, the mixture can proceed through an opening or openings in the reactor vessel and then directly into the gas cooling apparatus. The cooled mixture can then be directed to the catalyst separation apparatus by pipes or other suitable conduits.

DETAILED DESCRIPTION OF THE INVENTION

FIG. 1 shows a preferred embodiment of the reactor apparatus of this invention. In FIG. 1, reactor apparatus 1 is shown in cross-sectional view. Reactor apparatus 1 comprises a shell 10 suitably constructed of a material, as described above, that can withstand temperature and pressures used to conduct a desired chemical reaction. It is preferably constructed of a material that will withstand the chemical reactivity of the chemical compounds or other materials, such as catalyst, placed therein, or at least lined with a material that can withstand such chemical reactivity. For example, if the chemical reactants or chemical products present in the reactor during use, particularly at elevated temperatures, are corrosive, a material should be selected that will not corrode, or will not corrode rapidly under the reaction conditions. The reactor shell is suitably constructed of a material such as steel, for example, low alloy, carbon or stainless steel. Reactor 1 also comprises catalyst grid 12, gas cooling apparatus 20, means to separate entrained or suspended particles from a gas, such as series arranged gas cyclones 30, and optional heat transfer apparatus 40 for the fluidized catalyst bed. Preferably, the cross-section of reactor apparatus 1 perpendicular to the vertical axis of the reactor apparatus 1 is circular. The lower portion of the reactor, identified as DB or dense bed zone in FIG. 1, is generally cylindrical. The middle portion of the reactor, identified as DZ or disengaging zone in FIG. 1, comprises a lower conically shape portion and a cylindrical portion, indicated by marked sections A and B, respectively. The conical portion A is smaller in diameter at the location where it is connected to the DB zone and then widens to where it meets the cylindrical section B as shown in FIG. 1. The upper portion of the reactor, DP or dilute phase zone in FIG. 1, comprises a conical portion indicated by marked section C and a domed, hemispherical- or elliptical-capped, top portion, indicated by marked by section D. The conical portion C is greatest in diameter where it is in contact with cylindrical portion B and gradually narrows or tapers in diameter to where it meets domed portion D. The bottom of the reactor has a conical section 50.

Reactor 1 has a means for permitting gas or other reactants to enter the reactor. As shown in FIG. 1, 60 and 70 are inlets that can be used, for example, for the introduction of ammonia and molecular oxygen-containing gas, respectively. Depending on the specific chemical reaction to be conducted in the reactor apparatus 1, fewer inlets may be present or additional inlets for other reactants may be present. Inlets 60 and 70 are connected as shown in FIG. 1 to a means 80 and 90, respectively, for dispersing or distributing the reactants. The means for dispersing or distributing the reactants, for example reactant gases, also referred to herein as a reactant gas distribution system, can be any suitable means to disperse or distribute the reactant gas or gases. In the preferred embodiment of this invention, reactant gas distribution systems are used to disperse the reactant gas or gases, and they can be spargers or comprise a collection or network of pipes or other conduits fitted with one or more orifices or nozzles, or other means to disperse the gas or gases throughout, for example, the portion of the reactor 1 above grid 12. The preferred reactant gas distribution system for the reactor apparatus of this invention, as shown in FIG. 1 and in more detail in FIGS. 2 and 3, comprises a plurality of gas distribution tubes 82 and 92 and manifold tubes 80 and 90. Each of manifold tubes 80 and 90 are connected to distribution tubes, 82 and 92, respectively, and the distribution tubes have a plurality of gas delivery tubes 85 and 95 extending, respectively, therefrom down to near the top surface of grid 12. In the preferred embodiment, the gas delivery tubes from the distribution tubes for one of the reactant gases, for example ammonia gas, terminate at or near, preferably above, the holes in the grid, whereas the gas delivery tubes from the distribution tubes for the other reactant gas, for example molecular oxygen gas, terminate in a location above the grid and away from the holes in the grid. This arrangement is shown in plan view in FIG. 2 and in three-dimensional view in FIG. 3. A preferred grid in FIG. 2 and the detailed, three-dimensional drawing of a preferred reactant gas distribution system as shown in FIG. 3, are described in more detail below.

Reactant gas or gases can also enter reactor apparatus 1 through inlet 96. Reactant gas, preferably a reactant comprising propane, can enter reactor 1 through inlet 96 and pass into the DB zone of reactor apparatus 1 above grid 12 by passing through holes or other orifices in grid 12. In the preferred embodiment of this invention, grid 12 is generally a plate within the reactor apparatus and extending to the inside circumference of the reactor vessel as shown in FIG. 1 and comprising a collection of holes or orifices preferably spaced evenly about the area of the plate to allow a gas or other reactant to pass through the plate from the portion of the reactor apparatus under the plate to the portion of the reactor apparatus above the plate when the reactor apparatus is in the preferred vertical position. The holes or orifices can include tubular nozzles 11 extending below the grid plate. As will be described in more detail below, the portion of the reactor apparatus above the plate can contain a solid, particulate catalyst. During the operation of the reactor apparatus, gas passing through the holes or orifices in the plate of grid 12 enters a bed of the catalyst particles and fluidizes the catalyst particles located above the grid. Therefore, the holes or orifices in the plate forming the grid must be of a sufficient size to permit the passage of the reactant gas or gases, yet not too great a size to permit the particulate catalyst to fall through the holes to an appreciable extent. In the preferred embodiment, the nozzles 11 have an orifice located within the inner diameter of the nozzle and preferably at the end of the nozzle distal from where the nozzle connects with the grid. The orifice is of a size or diameter to provide for the desired pressure drop between the gas in the reactor below the grid and the gas above the grid, and to provide for the desired rate of gas flow through the nozzle and into the reactor space above the grid. Such a nozzle with an orifice within the nozzle is shown in detail in FIG. 3.

Figure 4:
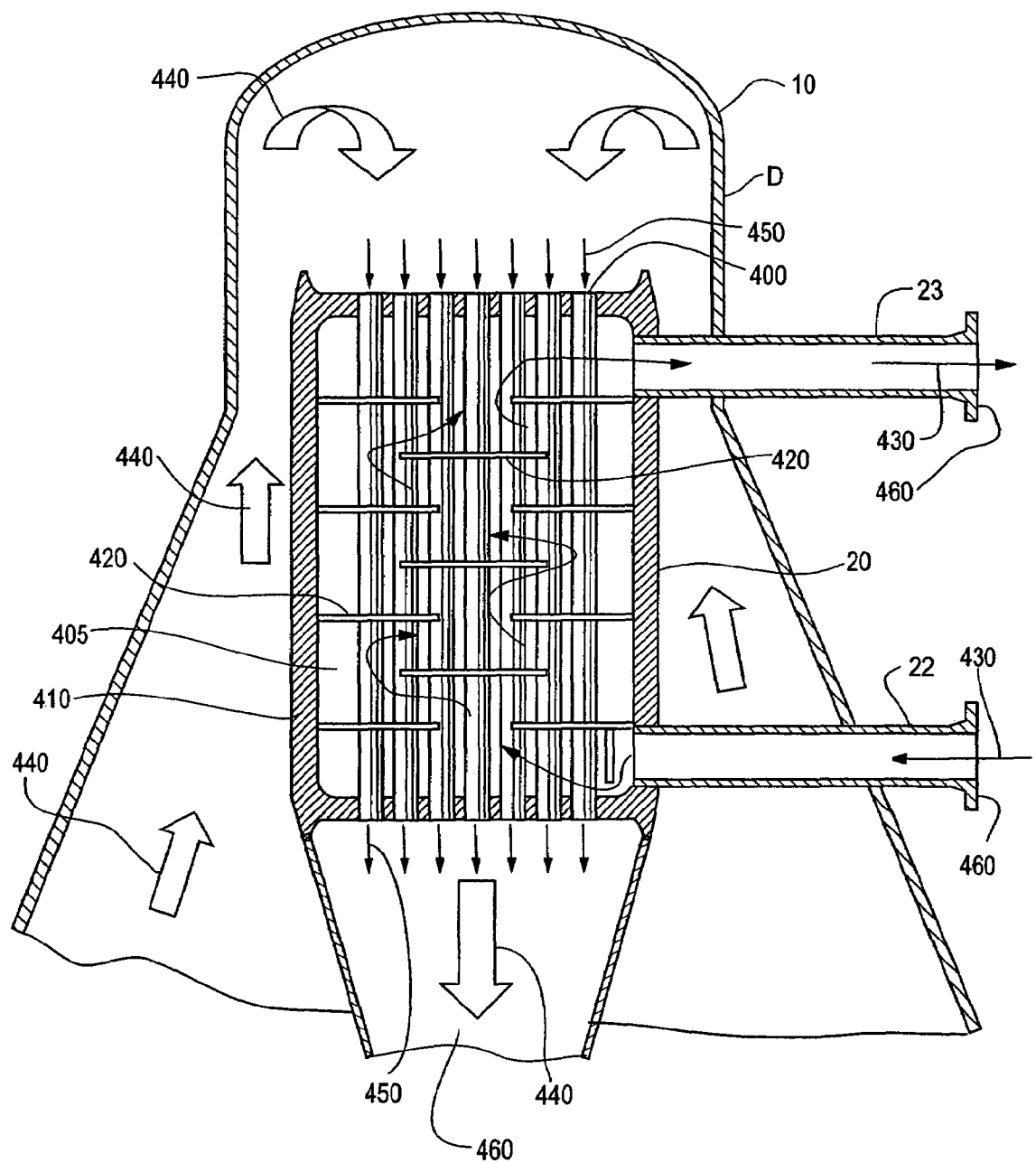
FIG. 4 shows in cross-sectional view a preferred gas cooler for use in a preferred reactor apparatus of this invention.
Figure 5:
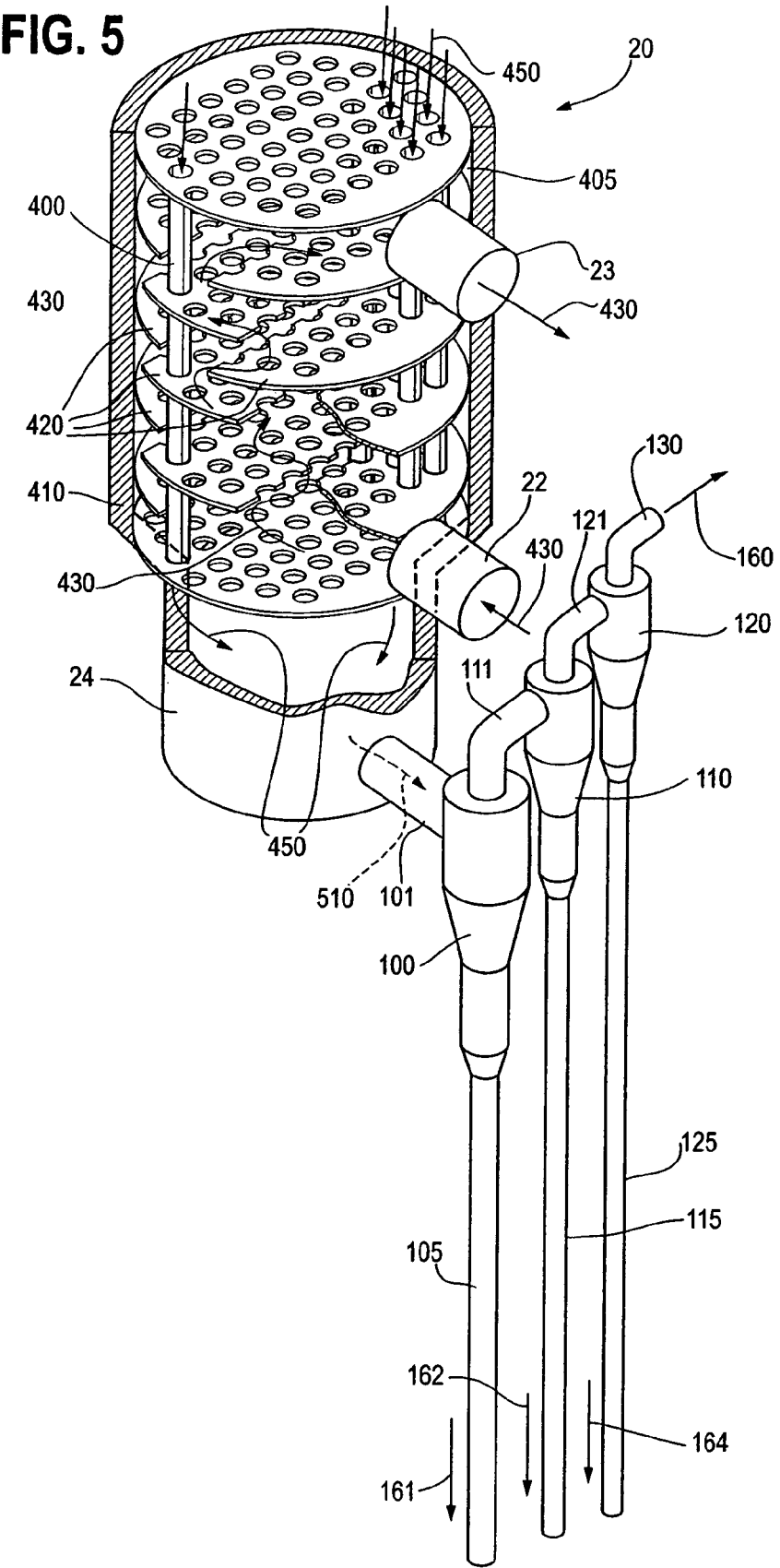
FIG. 5 is a three-dimensional view of a preferred gas cooler and series arranged gas cyclone separators for use in a preferred reactor apparatus of this invention.

Gas cooler 20 is any means that can be used to cool a gas. In the preferred embodiment of this invention, gas cooler 20 is a shell-and-tube type of cooler where, for example, gases comprising product and, if present, reactant gases and also containing suspended or entrained catalyst particles can pass through the gas cooler entering the cooler from the top, that is, the upper portion of gas cooler 20 shown in FIG. 1, and pass down through the cooler and exit the cooler at the bottom, that is, the lower portion of gas cooler 20 shown in FIG. 1, and enter the series arranged, gas cyclones 30 or other means for separating the cooled gas from suspended or entrained particulates such as catalyst particles. A cooling medium, such as water, steam or other suitable fluid, for cooling the gas passing through the tubes in such a shell-and-tube type cooler can enter and exit the cooler through flanged conduits 22 and 23, respectively. Cooled gas exiting the cooler passes into distributing means or plenum 24 located at the lower portion of gas cooler 20 before entering cyclones 30 or other means for separating suspended catalyst particles from the cooled gas. Gas cooling means 20 should be constructed, as with all the other components within the reactor apparatus 1, of a material that will withstand the conditions and chemical reactivity of the reactants and products within the reactor. A material such as steel, preferably low alloy, carbon or stainless steel can be used. Preferred cooler 20 is shown in greater detail in FIGS. 4 and 5, is described in more detail with respect thereto.

Gas cyclones 30 separate the product gas or gases exiting the gas cooler from suspended or entrained particles, such as catalyst particles. As shown in FIG. 1, more than one cyclone can be used. FIG. 1 shows three cyclones 100, 110 and 120 arranged in series. Cooled gas effluent from gas cooler 20 comprising gaseous product and any entrained or suspended catalyst particles enters first stage cyclone 100 through conduit 101. Gaseous effluent from cyclone 100 enters second stage cyclone 110 through conduit 111, and gaseous effluent from second stage gas cyclone 110 enters third stage gas cyclone 120 through conduit 121. Gaseous effluent from third stage gas cyclone 120 exits the reactor via flanged pipe 130 and can be directed to a separation and purification system for isolating product, such as acrylonitrile, from the gaseous effluent.

Each of cyclones 100, 110 and 120 have attached thereto diplegs 105, 115 and 125 respectively, which are conduits, for example pipes, that preferably extend down into the DB zone near the grid. Although not shown in FIG. 1, each of the diplegs preferably terminates in a means such as a deflector plate or flap valve, for preventing the upward flow of gas into the dipleg. The diplegs serve to direct any catalyst recovered by the gas cyclones to the lower portion of the reactor where the majority of the catalyst would be located. Although FIG. 1 shows one set of three cyclones in series arrangement, it is to be understood that each set can contain fewer or additional cyclones, for example 2 or 4 cyclones, and there can be multiple sets of such series arranged cyclones, for example 2 to 10 sets of such series arranged cyclones. FIG. 5 shows in more detail the internal portion of the preferred gas cooler and the arrangement of the cyclones. FIG. 5 will be described in more detail below. It is to be understood that other means for separating the catalyst particles from the gas can be used instead of cyclones, such as, for example, a filter system or a precipitator.

Although not shown in FIG. 1, the components such as the grid, gas cooler and cyclones can be supported securely in place by any suitable means such as support beams or other such devices.

Figure 2:
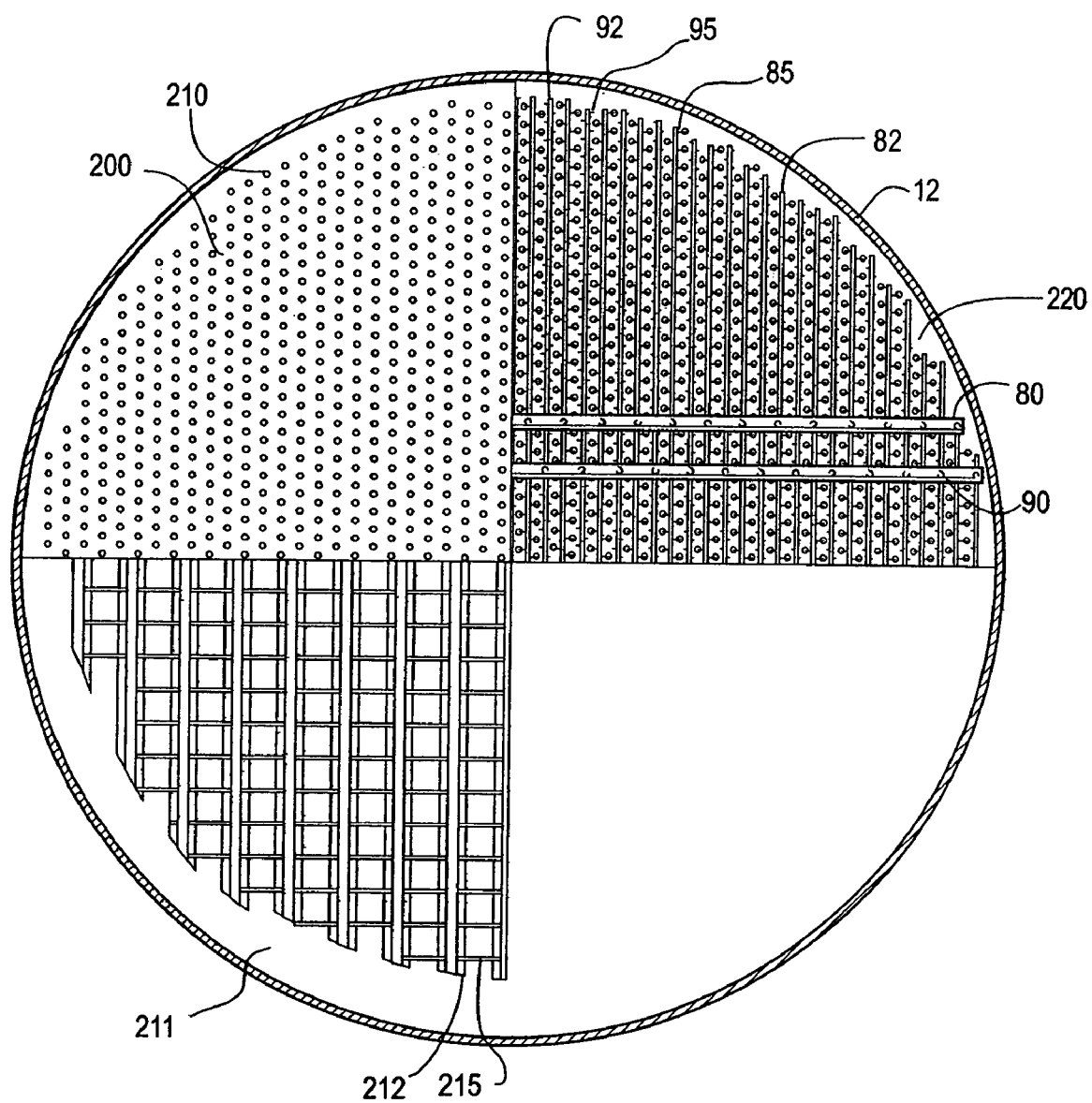
FIG. 2 shows in plan view a preferred grid for use in a preferred reactor apparatus of this invention.
Figure 3:
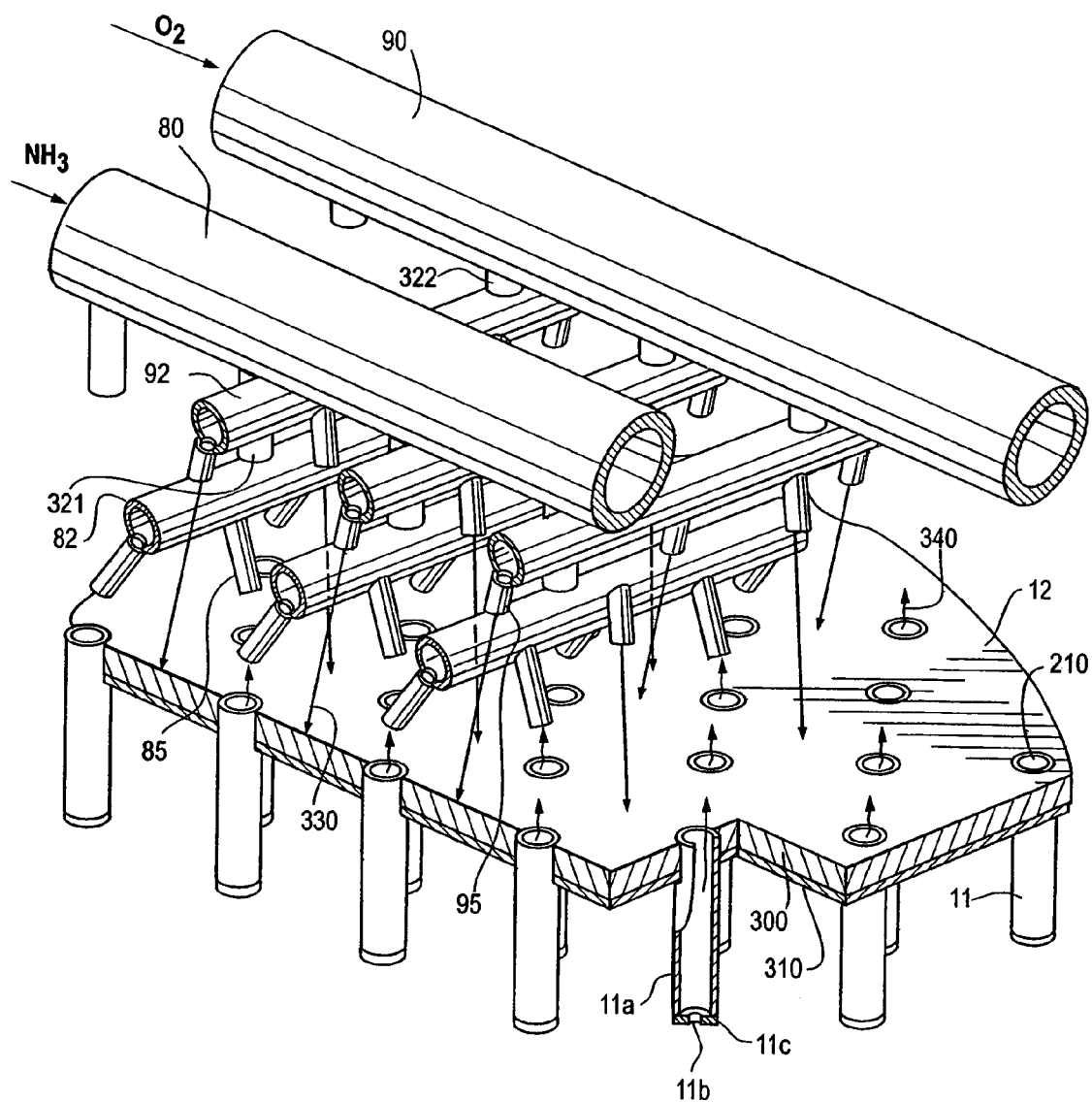
FIG. 3 shows in three-dimensional view a preferred reactant gas distribution system for use in a preferred reactor apparatus of this invention.

FIG. 2 is a plan view of a preferred grid and gas distribution system that can be used for a reactor apparatus of this invention. The view is from above the grid looking down when the grid is placed in the reactor apparatus and the reactor apparatus is in the preferred vertical position. Elements that are the same in FIGS. 1 and 2 are numbered the same for clarity. Although gas distribution system 220 and support beam lattice 211 is shown in quarter section, and grid section 200 is shown in half section, it is to be understood that each section extends over the entire area of the circular shaped grid shown in FIG. 2.

In FIG. 2, grid section 200 shows the plurality of holes 210 through the grid for permitting gas to pass from under the grid to a fluidized bed of catalyst particles located above the grid. The holes are evenly spaced from each other and arranged in evenly spaced rows. Holes in one row are positioned between the holes in an adjacent row. Section 211, which would be beneath grid section 200, shows a lattice of perpendicular support beams 212 and 215 used to support the grid. Section 220 shows the reactant gas distribution system having manifold tubes 80 and 90, gas distribution tubes 82 and 92 and gas delivery tubes, 85 and 95. As shown in FIG. 2, gas delivery tubes 85 extending from gas distribution tubes 82 are positioned so that the ends of the gas delivery tubes 85 where gas exits are positioned over the holes in grid section 200, and gas delivery tubes 95 extending from gas distribution tubes 92 are positioned so that the ends of the gas delivery tubes 95 where gas exits are away form the holes in grid 200.

FIG. 3 is a three-dimensional view of a section of a preferred grid and reactant gas distribution system useful in the reactor apparatus of this invention, and is also a three-dimensional view of a section of the gas distribution system shown in FIGS. 1 and 2. Elements in FIG. 3 that are the same in FIGS. 1 and 2 are numbered the same for clarity.

FIG. 3 shows grid 12 having refractory insulating material as a layer 300 over a metal grid plate with holes, 310.

Grid 12 has a plurality of holes 210 and nozzles 11 inserted in the holes 210. FIG. 3 shows that manifold tubes 80 and 90 are connected by a plurality of connecting tubes 321 and 322, respectively, to a plurality of gas distribution tubes 82 and 92, respectively. Distribution tube 82 and 92 are connected to a plurality of gas delivery tubes 85 and 95, respectively. Distal ends of gas delivery tubes 85 are positioned over the holes in the grid. Gas delivery tubes 95 are positioned so that gas exiting such tubes, as depicted by arrows 330, is directed to a location away from holes 210 in grid 12. Arrows 340 show the direction of a gas, such as a gas comprising propane, moving in an upward direction through holes 210. As shown in FIG. 3, and as an example, molecular oxygen-containing gas enters manifold tube 90, is directed through connecting tubes 322 to gas distribution tubes 92, then through gas delivery tubes 95, and is directed to a location on the grid away from where, for example, propane would be exiting through holes 210. Similarly, and also as an example, ammonia gas enters manifold tube 80, is directed through connecting tubes 321 to gas distribution tubes 82, then through gas delivery tubes 85, and is directed to a location on the grid directly over where a gas containing, for example, propane would be exiting through holes 210. Nozzle 11a in FIG. 3 shows the details of an orifice 11b in a cap 11c on the end of nozzle 11a distal from where the nozzle is attached to grid 12. Although not shown in FIG. 4, delivery tubes 85 and 95 can be attached, for example, welded, to distribution tube 82 and 92 respectively, over a hole in distribution tubes 82 and 92 that is a smaller diameter than the inside diameter of delivery tubes 85 and 95, thereby creating an orifice for reactant gases to pass through before entering delivery tubes from the distribution tubes.

FIG. 4 is a cross-sectional view of the upper section part D and including a portion of part C of the preferred vertically positioned reactor apparatus of FIG. 1 showing a preferred internal construction of gas cooler 20 and shell of reactor vessel 10. In gas cooler 20 a plurality of gas cooling tubes 400 pass through jacketed region 405. Jacket region 405 is defined by the outer wall 410 of gas cooler 20. Gas cooler 20 contains a plurality of baffles 420 to insure that cooling fluid passing through the jacked region 405 reaches all surfaces of gas cooling tubes 400. Cooling fluid enters jacked region 405 through flanged pipe 22 and exits through flanged pipe 23. Arrows 430 show the path of cooling fluid moving through the jacket region of gas cooler 20. Large arrows 440 show the flow of a mixture, for example, comprising product and, if present, reactant gases, as well as entrained or suspended catalyst particles first up past the side of gas cooler 20, then down through tubes 400 and out the bottom of tubes 400 into plenum 460. Arrows 450 show the path of that mixture through cooling tubes 400. Pipes 22 and 23 have flanges 460 for connecting pipes 22 and 23 to the cooling fluid system for providing and receiving cooling fluid circulated through gas cooler 20. Elements in FIG. 4 that are the same as in FIGS. 1-3 are numbered the same for clarity.

FIG. 5 is a cut-away, three-dimensional view of the preferred gas cooler 20, plenum 24 and an expanded view of gas cyclones 100, 110 and 120 that can be used in the reactor apparatus of this invention. Elements in FIG. 5 that are the same in FIGS. 1-4 are numbered the same for clarity. FIG. 5 in particular shows the internal arrangement of gas cooler 20 in detail. It shows the plurality of gas cooling tubes 400 passing through the jacked region 405. FIG. 5 in particular also shows the series arrangement of three gas cyclones 100, 110 and 120 used for separating entrained catalyst particles from the mixture of, for example, product and reactant gases and entrained catalyst particles, depicted by arrow 510 in FIG. 5, exiting plenum 25 and entering conduit 101.

The reactor apparatus in FIG. 1, and with reference thereto, is preferably operated in the following manner for the ammoxidation of propane with molecular oxygen-containing gas and ammonia gas to form acrylonitrile. A solid particulate catalyst, such as one or more catalysts known in the art useful for converting propane to acrylonitrile when heated in the presence of molecular oxygen and ammonia, for example, one or more of the catalysts described in the U.S. Patents relating to catalysts listed above, is contained in lower Dense Bed (DB) portion of reactor apparatus 1. The amount of catalyst present is preferably an amount that will fill the section of the reactor labeled DB when the reactor is in operation and the catalyst is in a fluidized state. Reactant gases such as ammonia and source of molecular oxygen enter reactor through inlets 60 and 70, respectively, and are distributed in the bottom of the reactor by a gas distributing means comprising manifold tubes 80 and 90, distribution tubes 82 and 92 and gas delivery tubes 85 and 95. Reactant propane and any recycle gases such as recycled propane enters reactor apparatus 1 through inlet pipe 96. By recycle gases we mean a gas that is recovered from the outlet of the reactor, for example, propane, and which is returned to the reactor as recycle to be used again in the process of converting propane to acrylonitrile. Other recycle gases may include one or more of molecular oxygen, carbon monoxide, carbon dioxide, and nitrogen. Reactant propane and any recycle gas flow through nozzles 11 in grid 12 and fluidize the particulate catalyst in the DB section of the reactor. In the dense, fluidized catalyst bed, most of the desired catalytic reactions occur where propane is converted to acrylonitrile and useful co-products such as hydrogen cyanide and acetonitrile. The ammoxidation reaction is exothermic. Cooling coil 40 is used to regulate the temperature of the fluidized catalyst bed by removing excess heat from the fluidized catalyst bed. The product and any remaining reactant gases pass through the dense bed and enter the disengaging zone (DZ) of the reactor shown as DZ in FIG. 1. The gases have catalyst particles from the fluidized catalyst bed suspended or entrained therein. In the disengaging zone, most of the suspended or entrained catalyst particles separate from the reactant and product gases and return to the dense bed zone by gravity. The expanded diameter of the DZ section of the reactor apparatus in FIG. 1 reduces the velocity of the gases traveling upward within the reactor apparatus thereby reducing the velocity of such gases in the disengaging zone and thereby facilitating the disengagement of a portion of the catalyst suspended or entrained therein. Product and reactant gases and remaining entrained or suspended catalyst particles pass up to the top of reactor into the dilute phase (DP) zone of the reactor and flow down into the top or upper portion of gas cooler 20 where the gases are cooled. Cooled gas still containing suspended or entrained catalyst particles exits the bottom or lower portion of cooler 20 and enter and then exit plenum 24 into first stage cyclone 100. FIG. 1, for clarity, shows only one group of three series-arranged cyclones. However, it is to be understood that plenum 24 can have a plurality of such cyclones or series-arranged cyclones connected thereto. Catalyst particles separated by cyclone 100 return to the dense bed portion of the reactor through dipleg 105. Effluent gas containing the product acrylonitrile and other product and reactant gases exit cyclone 100 and enter second stage cyclone 110 through conduit 111. Catalyst particles separated by cyclone 110 return to the dense bed portion of the reactor through dipleg 115. Effluent gas containing the product acrylonitrile and other product and reactant gases exit cyclone 110 and enter third stage cyclone 120 through conduit 121. In third stage cyclone 120 all or substantially all of the remaining catalyst particles entrained or suspended in the mixture comprising product and reactant gases are removed and are returned to the dense bed portion of the reactor by dipleg 125. Gases containing the product acrylonitrile and other product and reactant gases exit third stage cyclone and enter product outlet 130. Although a dense bed of catalyst is not depicted in FIG. 1, arrows depict the flow of reactant and product gases first with and then without entrained catalyst particles. Thus, arrow 140 shows the upward direction of reactant and product gases through the DB zone of the reactor, arrow 142 and 144 show the upward motion of reactant and product gases containing suspended or entrained catalyst particles through the disengaging and dilute phase zones, DZ and DP, respectively, and passing the outside of gas cooler 20. In the expanded DZ zone, the reactant and product gases containing suspended or entrained catalyst particles, diminish in velocity thereby permitting the disengagement of a portion of the catalyst particles from the gas. Arrows 146 show the turning of the direction of reactant and product gas mixture still containing some suspended or entrained catalyst particles so that the direction of flow of the gas is downward. Arrows 148 and 150 show the mixture of reactant and product gases and suspended or entrained catalyst particles passing through gas cooler 20 and into plenum 24, respectively. Horizontal arrows in conduits 101, 111, and 121 show the path of the reactant and product gases through cyclones, 100, 110 and 120, and arrow 160 shows the direction of flow of the mixture of reactant and product gases, after separation of suspended catalyst from the gases, exiting reactor apparatus 1 through flanged exit pipe 130. Arrows pointing downward within cyclones 100, 110 and 120 show the direction of flow of catalyst particles separated in gas cyclones 100, 110 and 120. Arrows 161, 162 and 164 show the downward movement of separated catalyst particles within diplegs 105, 115 and 125. Cyclone 100, first cyclone in series-arranged cyclones, is preferably larger than the cyclones later in the series of series-arranged cyclones such as cyclones 110 and 120. The first-stage cyclone in the series-arranged cyclones is preferably larger so it can accomplish the major amount of catalyst separation. Similarly, the dipleg for the first cyclone is preferably of greater cross-sectional size, for example, greater diameter, than the diplegs for the subsequent cyclones in the series-arranged cyclones to accommodate larger amounts of catalyst particles flowing therethrough. Arrow 170 shows the direction of flow of heat transfer medium or cooling fluid into flanged pipe 22 and into shell of gas cooler 20. Arrows 122 show the preferred winding path of cooling fluid as it passes through the shell of gas cooler 20 and arrow 174 shows the direction of flow of cooling fluid as it exits gas cooler through flanged pipe 23.

FIGS. 6 through 11 show in simplified, schematic drawings, examples of embodiments of the reactor apparatus of this invention.

Figure 6:
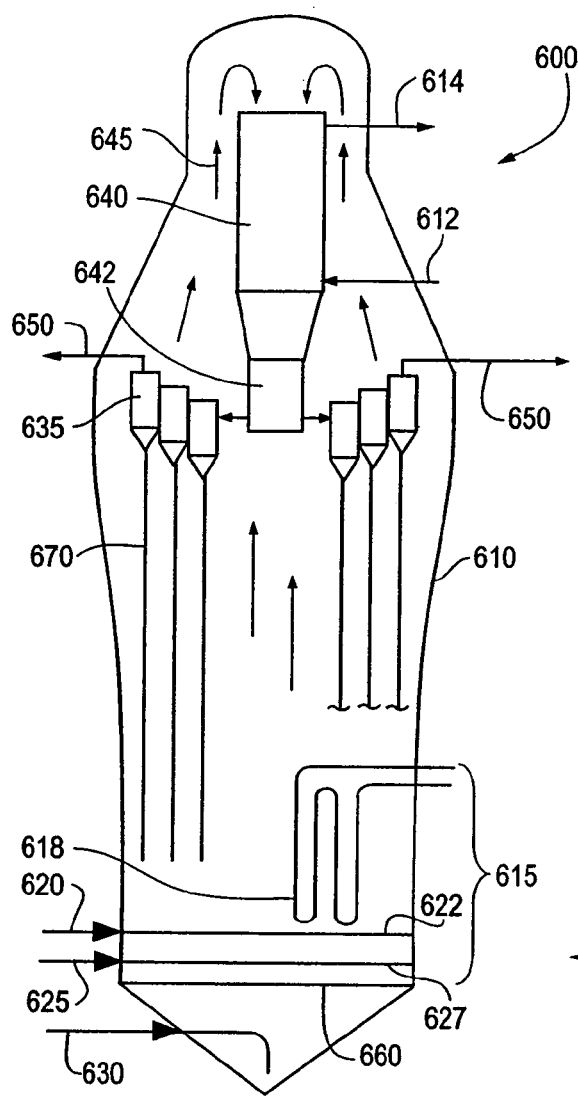
FIGS. 6 through 11 are each schematic drawings of examples of embodiments of the reactor apparatus of this invention.

FIG. 6 shows in a simplified schematic drawing the reactor of FIG. 1 except that it shows two groups of series-arranged cyclones and a separate product gas outlet for the second set of series-arranged cyclones. In FIG. 6, reactor 600 has reactor shell 610, dense fluidized catalyst bed zone depicted by bracket 615 (for clarity, catalyst bed not shown), heat transfer apparatus 618 for regulating the temperature of the fluidized catalyst bed, reactant gas inlets 620 and 625 for supplying, for example, oxygen-containing gas and ammonia to the reactor, gas distribution systems 622 and 627 for distributing, for example, oxygen-containing gas and ammonia, reactor gas inlet 630 used, for example, for adding propane to the reactor, catalyst separation apparatus 635, shown, for example, as cyclones, gas cooler 640 shown, for example, as a single-pass, shell-and-tube cooler, having inlet 612 and outlet 614 pipes for circulating cooling fluid through the gas cooler, plenum 642, arrows 645 showing the path of flow of the mixture of product and, if present, reactant gases with and, after passing through catalyst separation apparatus, without suspended or entrained catalyst particles, product gas or gases exit pipes 650, grid 660, and diplegs 670 for returning catalyst particles to the fluidized catalyst bed.

Elements of the reactor apparatus shown in FIGS. 7 through 11 that are not indicated by a number but are drawn or depicted the same as shown in FIG. 6, are, unless stated otherwise, the same elements as described with respect to FIG. 6. All the reactor apparatus shown in FIGS. 6-11 are depicted in a vertical position.

Figure 7:
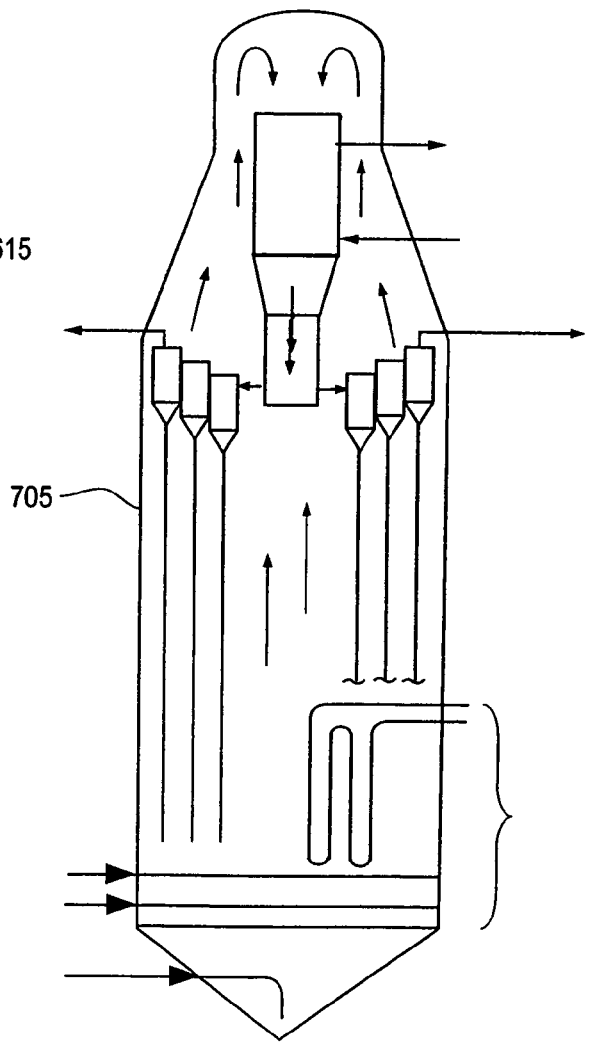

FIG. 7 shows an embodiment of a reactor apparatus of this invention that is the same as the reactor shown in FIG. 6 except that in the embodiment shown in FIG. 7, the reactor shell does not have a middle section 705 which is expanded relative to the lower DB section or zone. For the same chemical reaction and reaction conditions such as pressure, temperature and gas flow rates for reactant and product gases, the reactor apparatus shown in FIG. 7 can have a dense phase zone and disengaging zone diameter that is approximately equal to the diameter of the expanded middle section or disengaging zone of the reactor apparatus shown in FIG. 6. For such reactors, the velocity of the mixture comprising product and, if present, reactant gases, and containing entrained catalyst particles entering the dilute phase zone of each reactor would be similar and the amount of suspended or entrained catalyst particles would also be similar.

Figure 8:
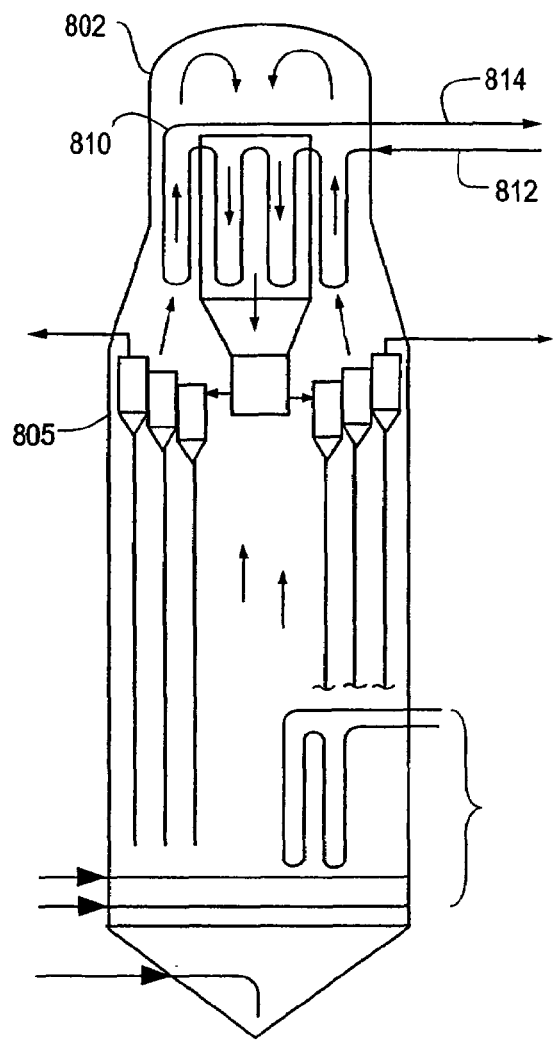

FIG. 8 shows an embodiment of a reactor apparatus of this invention that is the same as the reactor apparatus shown in FIG. 7 except that in the embodiment shown in FIG. 8 the top section of the reactor shell 802 in proportion to the middle section 805 has a larger diameter, and the reactor contains a cooling coil 810, such as for example, a finned tube cooling coil, having inlet 812 and outlet 814 pipes for cooling fluid to circulate within the coil. The cooling coil is used as a gas cooler in addition to, for example, the shell-and-tube gas cooler used to cool the mixture of product and, if present, reactant gases containing suspended or entrained catalyst particles before separating the catalyst particles from the mixture of gas or gases and catalyst particles.

Figure 9:
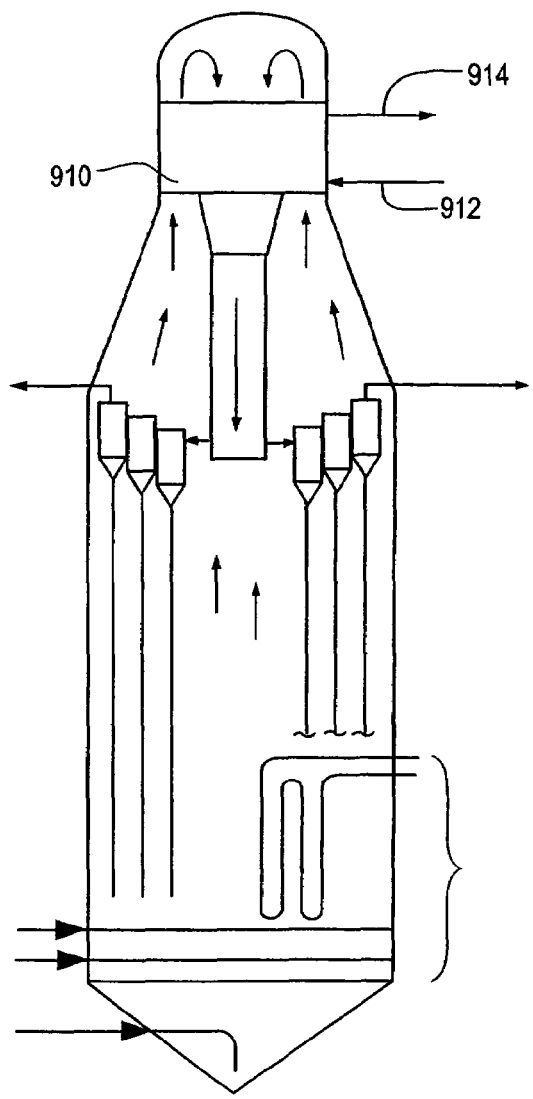

FIG. 9 shows and embodiment of the reactor apparatus of this invention that is the same as the reactor apparatus shown in FIG. 8 except that the cooling coil and the single-pass gas cooler are replaced with a two-pass gas cooler 910, such as a two-pass shell-and-tube cooler. In the two-pass cooler, the mixture comprising product and, if present, reactant gases containing suspended or entrained catalyst particles passes through the two-pass cooler as the mixture travels vertically upwards within the reactor and then passes through the cooler again on the downward path as shown by the arrows in FIG. 9. Two-pass cooler 910 has inlet 912 and outlet 914 pipes for cooling fluid to circulate through the cooler.

Figure 10:
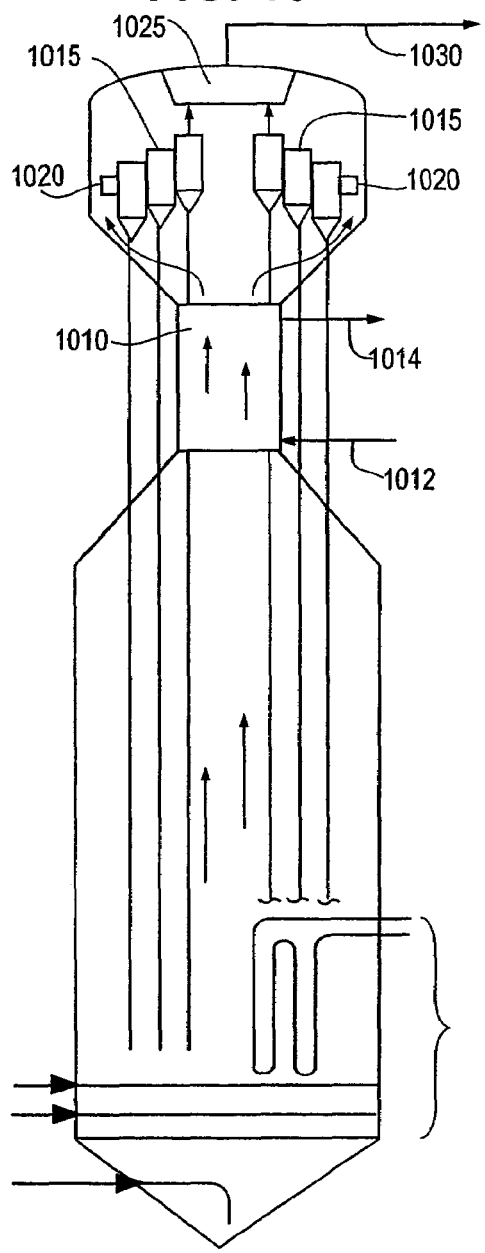

FIG. 10 shows an embodiment of the reactor apparatus of this invention having a single-pass, upflow gas cooler 1010, such as, for example, a single-pass, upflow shell-and-tube gas cooler. In this embodiment, the mixture comprising product and, if present, reactant gases and containing suspended or entrained catalyst passes through the upflow gas cooler 1010 as the mixture travels in an upward direction within the reactor. After exiting the cooler the mixture enters a catalyst separation apparatus such as series-arranged cyclones 1015 through openings 1020 in the first-stage cyclone of the series-arranged cyclones. After passing through the series-arranged cyclones, the mixture of product and, if present, reactant gases enters plenum 1025 before exiting the reactor through pipe 1030. Single-pass, upflow cooler 1010 has inlet 1012 and outlet 1014 pipes for cooling liquid or other suitable fluid to circulate through the cooler.

Figure 11:
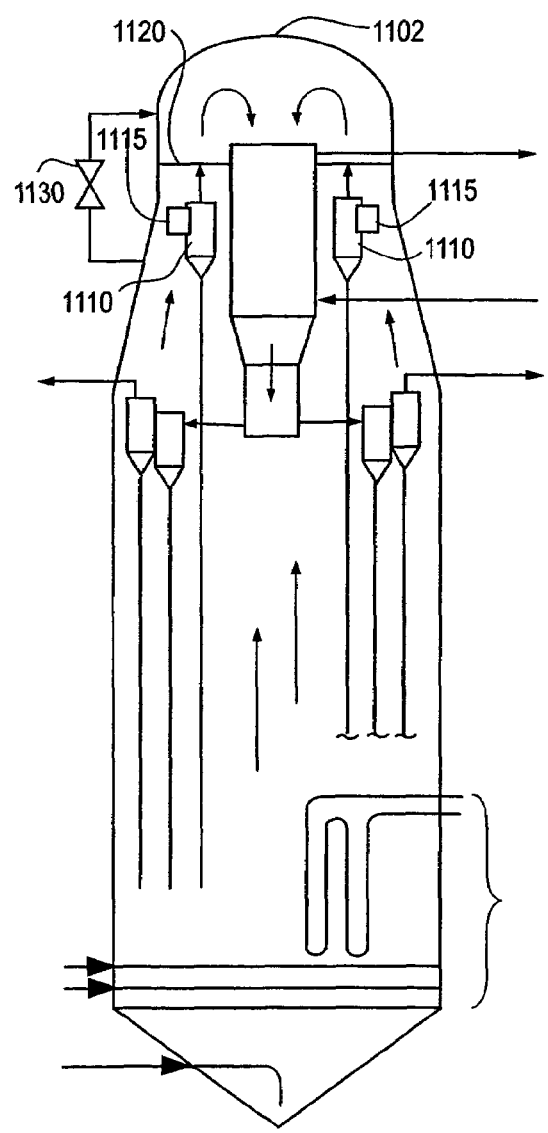

FIG. 11 shows an embodiment of the reactor of this invention that is the same as the reactor shown in FIG. 8 except that it does not have cooling coil 810 and it includes a "rough-cut" catalyst separation apparatus 1010 such as, for example, cyclones. Rough-cut separation apparatus is used to remove part of the catalyst from the mixture comprising product and, if present, reactant gases and containing suspended or entrained catalyst. Thus, the rough-cut catalyst separation apparatus can accomplish the same or similar disengagement of the catalyst particles from such mixture of gases that is accomplished by the expanded disengaging zone shown in the reactors shown in FIGS. 1 and 6. In the reactor of FIG. 11 the mixture comprising product and, if present, reactant gases and containing suspended or entrained catalyst particles enters the intake 1115 of the cyclones 1110. Separated catalyst particles return to the dense phase catalyst bed through the dipleg attached to cyclones 1110. The mixture comprising product and, if present, reactant gases, now containing a reduced level of suspended or entrained catalyst, enters the top section 1102 of the reactor through plate 1120. Plate 1120 isolates the top section of the reactor 1102 from the rest of the reactor and does not permit the mixture comprising the product and, if present, reactant gases and containing suspended or entrained catalyst from entering the top section of the reactor except by passing through cyclones 1110 or through bypass valve 1130 if the bypass valve is in the open position. Bypass valve 1130 can be use to regulate the amount of the mixture of product and, if present, reactant gases and containing the suspended or entrained catalyst mixture that passes through cyclones 1110.

Although the reactor apparatus of this invention can be used for the ammoxidation of propane to form acrylonitrile, and has been described herein with respect to such use, it is to be understood that its use is not so limited and it can be used to conduct other chemical transformation reactions. For example, it can be used to convert other hydrocarbons, either saturated, such as propane, n-butane or isobutane, or unsaturated, such as propylene, or isobutylene, to their corresponding unsaturated nitrites, that is, acrylonitrile or methacrylonitrile. It can also be used, for example, for the oxidation of benzene or butane to maleic anhydride, the catalytic cracking of crude oil to form gasoline and other hydrocarbons, the coking of residua, coke gasification and the like catalyzed chemical transformation reactions.

Only certain embodiments of the invention have been set forth and alternative embodiments and various modifications will be apparent from the above description to those of skill in the art. These and other alternatives are considered equivalents and within the spirit and scope of the invention.

U.S. Provisional Patent Application Ser. No. 60/469,608, filed on May 9, 2003, is incorporated by reference herein in its entirety.

That which is claimed is:

1. A reactor apparatus for the manufacture of acrylonitrile with decreased afterburning comprising:

a reactor vessel defining a dense bed zone, a catalyst disengaging zone, and a dilute phase zone; wherein the dense bed zone contains a fluidized bed of particulate catalyst and, optionally, a heat transfer apparatus located within the fluidized bed of particulate catalyst; wherein the catalyst disengaging zone is positioned above the dense bed zone for separating and returning a first portion of entrained catalyst in a product gas mixture to the dense bed zone; and wherein the dilute phase zone is positioned above the catalyst disengaging zone, the dilute phase zone being defined in part by a domed hemispherical-or elliptical-capped top portion of the reactor vessel, the diameter of the top portion being smaller than the diameter of the disengaging zone; a grid positioned within the reactor vessel, below the fluidized bed of particulate catalyst at least one gas distribution system for supplying a reactant gas to the fluidized bed of particulate catalyst, the at least one gas distribution system being postioned near the upper surface of the grid; at least one gas inlet supplying a reactant gas to the fluidized bed of particulate catalyst, the at least one gas inlet being positioned below the grid and within a conically shaped bottom of the reactor vessel; a gas cooler postioned at least partially within the top portion of the dilute phase zone, for cooling the product gas mixture containing a second portion of entrained catalyst separation apparatus for separating the second portion of entrained catalyst from the product gas mixture, the catalyst separation apparatus being positioned within the reactor vessel and downstream from the gas cooler such that the product gas mixture containing the second portion of entrained catalyst is transported from the gas cooler to the catalyst separtion apparatus; means for returning separated catalyst from the catalyst separation apparatus to the dense bed zone; and at least one gas outlet for discharging the separated product gas mixture from the reactor vessel, the at least one gas outlet being positioned at the dilute phase zone.

2. The reactor apparatus of claim 1 wherein the horizontal cross-section of the reactor vessel is circular.

3. The reactor apparatus of claim 1 wherein the diameter of the disengaging zone is greater that the diameter of the dense bed zone.

4. The reactor apparatus of claim 1 wherein the gas cooler comprises a shell-and-tube gas cooler.

5. The reactor apparatus of claim 4 wherein the shell-and-tube gas cooler is selected from the group consisting of a single-pass, upflow shell-and-lube gas cooler, a single pass, downflow shell-and-tube gas cooler, a two-pass shell-and-lube gas cooler and any combination thereof.

6. The reactor apparatus of claim 1 wherein the catalyst separation apparatus is selected from the group consisting of a filter, a membrane, a screen, a cyclone and any combination thereof.

7. The reactor apparatus of claim 1 wherein the catalyst separation apparatus comprises a cyclone.

8. The reactor apparatus of claim 1 wherein the catalyst separation apparatus comprises at least one group of series-arranged cyclones located within the reactor vessel.

9. The reactor apparatus of claim 1 wherein the grid comprises a plurality of holes.

10. The reactor apparatus of claim 9 wherein the grid comprises a layer of insulating material.

11. The reactor apparatus of claim 1 wherein the at least one gas distribution system comprises at least one manifold tube, a plurality of distribution tubes connected to at least one manifold tube and a plurality of delivery tubes connected to each distribution tube, wherein a gas directed into a manifold tube will flow to the distribution tubes and then to and exit from the delivery tubes.

12. The reactor apparatus of claim 11 wherein the at least one gas distribution system comprises at least one insulated manifold tube.

13. The reactor apparatus ot claim 1 wherein the at least one gas distribution system comprises at least one manifold tube, a plurality of distribution tubes connected to at least one manifold tube and a plurality of delivery tubes connected to each distribution tube, wherein a gas directed into the manifold tube will flow to the distribution tubes and then to and exit from the delivery tubes, the delivery tubes having a first end attached to a distribution tube and a second, opposite end, wherein at least a portion of the second ends of the delivery tubes are located above a hole in the grid, and at least a portion of the second ends of the delivery tubes are located away from a hole in the grid.

14. The reactor apparatus of claim 13 wherein the delivery tubes having second ends located above a hole, and the delivery tubes having second ends located away from a hole, are connected to separate distribution tubes.

15. The reactor apparatus of claim 14 wherein the separate distribution tubes are connected to separate manifold tubes.

16. The reactor apparatus of claim 1 wherein the gas cooler comprises a two-pass gas cooler.

* * * * *